(12) United States Patent
Jacobs et al.

(10) Patent No.: US 12,016,712 B2
(45) Date of Patent: Jun. 25, 2024

(54) IDENTIFIABLE ANTI-SCATTER GRID FOR A RADIOGRAPHIC IMAGING DEVICE

(71) Applicant: KONINKLIJKE PHILIPS N.V., Eindhoven (NL)

(72) Inventors: Johannes Wilhelmus Maria Jacobs, Boxtel (NL); Lester Donald Miller, Hudson, OH (US); Nishant Singh, Son en Breugel (NL); Bernd Menser, Hauset (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 18/028,045

(22) PCT Filed: May 25, 2022

(86) PCT No.: PCT/EP2022/064139
§ 371 (c)(1),
(2) Date: Mar. 23, 2023

(87) PCT Pub. No.: WO2022/248519
PCT Pub. Date: Dec. 1, 2022

(65) Prior Publication Data
US 2024/0108297 A1 Apr. 4, 2024

Related U.S. Application Data

(60) Provisional application No. 63/193,504, filed on May 26, 2021.

(30) Foreign Application Priority Data

Jul. 27, 2021 (EP) .................................... 21187896

(51) Int. Cl.
*G21K 1/02* (2006.01)
*A61B 6/00* (2006.01)
(Continued)

(52) U.S. Cl.
CPC .......... *A61B 6/4291* (2013.01); *A61B 6/4494* (2013.01); *B22F 10/28* (2021.01)

(58) Field of Classification Search
CPC .......... G21K 1/04; G21K 1/025; G21K 1/043; G21K 1/046; G21K 1/067; G21K 1/10;
(Continued)

(56) References Cited

U.S. PATENT DOCUMENTS

| 7,113,615 B2 | 9/2006 | Rhoads |
| 8,233,967 B2 | 7/2012 | Hempel |

(Continued)

FOREIGN PATENT DOCUMENTS

| JP | 2002186613 A | 7/2007 |
| JP | 2012192031 A | 10/2021 |

(Continued)

OTHER PUBLICATIONS

PCT International Search Report, International application No. PCT/EP2022/064139, dated Sep. 21, 2022.

(Continued)

*Primary Examiner* — Don K Wong
(74) *Attorney, Agent, or Firm* — Larry Liberchuk

(57) ABSTRACT

The present invention provides methods and devices for making an anti-scatter grid for a radiographic imaging device identifiable. A method for providing an anti-scatter grid (100) for a radiographic imaging device comprises forming, by an additive manufacturing process, a grid pattern (110) in accordance with a product specification of the anti-scatter grid (100) to be provided; and forming, by an additive manufacturing process, a number of structural modifications (121) in or at the grid pattern in a manner making the number of structural modifications (121) image-based recognizable when the anti-scatter grid (100) is viewed according to its intended use in a viewing direction (Continued)

from a radiation source of the radiographic imaging device, and in a unique identification pattern (120) creating a unique identifier to make the anti-scatter grid to be provided identifiable among one or more others.

14 Claims, 4 Drawing Sheets

(51) Int. Cl.
*A61B 6/42* (2024.01)
*B22F 10/28* (2021.01)

(58) Field of Classification Search
CPC ...... G21K 5/04; G21K 2201/067; G21K 1/02; A61B 6/032; A61B 6/4035; A61B 6/06; A61B 6/4064; A61B 6/48; A61B 6/483; A61B 6/08; A61B 6/4291; G01N 2223/316; G01N 2223/051; G01N 2223/05; G01N 2223/053; G01N 2223/063; G01N 2223/064; G01N 23/20075; G01T 1/00
See application file for complete search history.

(56) References Cited

U.S. PATENT DOCUMENTS

| | | | |
|---|---|---|---|
| 9,062,965 | B2 | 6/2015 | Yoshida |
| 9,179,886 | B2 | 11/2015 | Stagnitto |
| 9,281,163 | B2 | 3/2016 | Routh, Jr. |
| 11,103,201 | B2 | 8/2021 | Du |
| 11,211,180 | B2 * | 12/2021 | Sharpless .......... B29C 45/14065 |
| 2009/0003530 | A1 | 1/2009 | Van Vroonhoven |
| 2012/0053680 | A1 | 3/2012 | Bolling et al. |
| 2012/0195404 | A1 | 8/2012 | Omura |
| 2015/0115494 | A1 | 4/2015 | Deych |
| 2017/0213116 | A1 | 7/2017 | Kieser |

FOREIGN PATENT DOCUMENTS

| | | |
|---|---|---|
| WO | WO2008007309 A1 | 1/2008 |
| WO | WO2020069950 A1 | 4/2020 |

OTHER PUBLICATIONS

Suzuki M. et al., "Number of Detectable Gradations in X-Ray Photographs of Cavities Inside 3-D Printed Objects", IEICE Transactions Information & System, vol. E100-D, No. 6, pp. 1364-1367, Jun. 2017.

* cited by examiner

IDENTIFIABLE ANTI-SCATTER GRID FOR A RADIOGRAPHIC IMAGING DEVICE

FIELD OF THE INVENTION

The present invention relates to radiographic imaging, and in particular to a method for providing an anti-scatter grid for a radiographic imaging device, a method for making a specific anti-scatter grid identifiable among one or more others, an anti-scatter grid for a radiographic imaging device, and a device for identifying a specific anti-scatter grid among one or more others.

BACKGROUND OF THE INVENTION

US 2017/0213116 A1 describes a method of inserting a data structure into a component using a 3D printer is provided. The method includes providing the data structure having at least one structural parameter associated with the component, converting the data structure into indicia representative of the data structure, and manufacturing the component containing the indicia.

WO 2008/007309 A1 describes a grid for selective transmission of electromagnetic radiation, particularly X-ray radiation, that has at least one structural element that was built by means of selective laser sintering of an essentially radiation-opaque powder material.

In radiographic imaging, e.g. in medical and/or industrial radiography, anti-scatter grids are used for reducing radiation scatter created in a radiographic exposure reaching a detector of a radiographic imaging device. Thereby, the anti-scatter grid is placed between a subject and the detector during the exposure. Such an anti-scatter grid may be manufactured by using an additive manufacturing process, such as 3D printing. During manufacturing, in order to provide product identification, a post-processing step of laser engraving may be performed, which adds a unique code on the 3D printed product. This post-processing step is cumbersome as it takes time that extends the overall manufacturing time. Further, it can lead to product errors, and it may introduce product damage or additional defects, which reduces overall production yield. Also, product tracing across the complete supply chain from manufacturer to end-user may be not transparent, and may lead to confusion and errors.

SUMMARY OF THE INVENTION

There may, therefore, be a need for an improved product identification of an anti-scatter grid. The invention is defined by the independent claims. Advantageous embodiments are defined by the dependent claims.

According to a first aspect, there is provided a method for providing an anti-scatter grid for a radiographic imaging device. The method comprises the steps of:
 forming, by an additive manufacturing process, a grid pattern in accordance with a product specification of the anti-scatter grid to be provided; and
 forming, by the additive manufacturing process, a number of structural modifications in or at the grid pattern in a manner making the number of structural modifications image-based recognizable when the anti-scatter grid is viewed according to its intended use in a viewing direction from a radiation source of the radiographic imaging device, and in a unique identification pattern creating a unique identifier to make the anti-scatter grid to be provided identifiable among one or more others.

In this way, a well-defined unique identifier, which may also be referred to as kind of or a well-defined watermark consisting of the number of structural modifications. This allows a specific anti-scatter grid to be uniquely identified among one or more others even if these are of the same type. The watermark can directly be embedded, in a structural, i.e. physical, manner, into the anti-scatter grid structure. Advantageously, this is performed directly during the manufacturing process of the actual anti-scatter grid, thereby omitting an additional post-processing step, such as laser engraving or the like, for making the product identifiable by a post-processed product code or the like. Thereby, the number of structural modifications is arranged and/or formed so as to not disturb functionality or operation of the anti-scatter grid. Furthermore, the anti-scatter grid may be identified from a direction, in particular a viewing direction, even in a position and/or orientation corresponding to its intended use, i.e. installed ready for imaging operation. This may even be done by the radiographic imaging device with or in which the anti-scatter grid is to be used itself.

As used herein, the additive manufacturing process may be broadly understood as any three-dimensional (3D) printing technique suitable to manufacture the anti-scatter grid. For example, the additive manufacturing process may be direct metal laser sintering (DMLS), selective laser melting (SLM), selective laser sintering (SLS), electron-beam melting (EBM), or the like. This is not limited herein.

Further, as used herein, the grid pattern extends two-dimensionally (2D) in a plane, e.g. x-y plane, with x as an outer edge and y as another outer edge, and has a thickness in a direction perpendicular thereto, e.g. z-direction. The grid pattern may comprise, for example, a plurality of alternating parallel strips or walls, wherein a manufacturing material may be selected from e.g. tungsten, lead, etc., and a radiolucent substance, such as a plastic, carbon fibre, aluminum, paper, etc. The outer edge(s) may also be referred to as periphery of the anti-scatter grid.

As used herein, the product specification may comprise information about a structure of the anti-scatter grid, e.g. dimensions, arrangement of walls, choice of materials, etc. Thereby, the product specification may define a specific type of anti-scatter grid and/or an anti-scatter grid that is dedicated to a specific radiographic imaging device.

Further, as used herein, the number of structural modifications may also be referred to as a number of intended structural modifications at a corresponding number of locations within the actual grid pattern that is overall manufactured according to the product specification, wherein the number of intended structural modifications may have either no or very little effect on the specified function of the anti-scatter grid, e.g. due to its only slight modification, or the effect on the anti-scatter grid may be compensated by corresponding calibration data or the like, associated with the specific anti-scatter grid. In other words, the number of structural modifications may be understood as being intentional, targeted, allowing to create a required number of unique combinations, codes or identifiers to be generated, and/or to ensure reliable visual recognition of the unique identification pattern.

As used herein, the unique identification pattern may be understood as some kind of watermark and creates a unique identifier, preferably in a one-to-one correspondence with a specific anti-scatter grid. The unique identification pattern may be comparable, at least in its functionality, with an QR-code, or the like. It is noted that the unique identification pattern may be read-out by e.g. a suitable code reader, an optical code reader, by utilizing a device according to the fourth aspect, a radiographic imaging device, or the like.

It is noted that the forming of the grid pattern and the forming of the number of structural modifications may be performed simultaneously, overlapping in time, alternately, or sequentially, according to the capabilities of the additive manufacturing process.

Further, it is noted that the forming of the grid pattern and the forming of the number of structural modifications do not necessarily have to use the same additive manufacturing process, but, optionally, for each additive manufacturing process a separate process can be used that differs from the other. For example, DMLS can be used for one forming process and selective laser sintering can be used for the other, and any known additive manufacturing process may be suitable, where this is not limited herein.

The radiographic imaging device, as used herein, may be broadly understood as an imaging device using a radiation source and/or an imaging technique using X-rays, gamma rays, or similar ionizing radiation and non-ionizing radiation to view or illustrate an internal form of an object. For example, the radiographic imaging device may be used in medical radiography, e.g. for diagnostic and/or therapeutic purposes, in industrial radiography, in in airport security, or the like. This is not limited herein.

Further, it is noted that each identification pattern has its unique combination formed from the number of modifications, so that no identification pattern is the same as the others, but differs from all the others in at least one combination point, i.e. in at least one structural modification, and is thus uniquely identifiable. Thereby, each of the number of modifications may be varied in e.g. its location, dimensions, shape and/or type, etc.

According to an embodiment, the number of structural modifications may be formed to be recognizable by forming at least a part of the number of structural modifications at one or more walls and/or surfaces forming the grid pattern. For example, the number of structural modifications may be formed by one or more of a local variation of a wall thickness, a local shift of a wall position, a local addition of a well-defined protrusion in, on top, or at bottom of a wall, a local removal of small well-defined structures from grid structure, a local application of small well-defined surface modification, e.g. roughness, etc., of a wall, a local application of a specific structure element, e.g. pinholes, cross hairs, etc., with a well-defined shape and dimensions outside an active grid pattern area, e.g. a circumferential edge of the anti-scatter grid, which runs in the plane in which the anti-scatter grid extends two-dimensionally, and a local application of an amount of second 3D material different to a first 3D material used to form grid pattern, wherein a quantity proportion of the second 3D material to the grid pattern is less than a quantity proportion of the first 3D material. In this way, the overall function of the anti-scatter grid is not disturbed by the number of structural modifications, wherein all these modification options can be applied during the forming process without requiring post-processing.

It is noted that, within this description, the wall may be a single wall, wherein the grid pattern is formed by a plurality of walls. Further, each of the number of structure modifications may be formed at more than one wall at the same time. Further, as used herein, the wall may also be referred to as a septa wall, which is to be understood as a wall diving a cavity or structure forming the grid pattern into smaller ones.

In an embodiment, the number of structural modifications may at least partly be formed by locally shifting one or more walls forming the grid pattern. For example, a section of a wall may be brought out of alignment with adjacent sections so that this is visually recognizable. In this way, the overall function of the anti-scatter grid is not disturbed by the number of structural modifications, wherein all these modification options can be applied during the forming process without requiring post-processing.

According to an embodiment, the number of structural modifications may at least partly be formed by forming a local variation of thickness of one or more walls forming the grid pattern. For example, an additional amount of material may be, preferably slightly, thickened at the corresponding location. Preferably, the additional amount of material may be located in a corner between two walls. In this way, the overall function of the anti-scatter grid is not disturbed by the number of structural modifications, wherein all these modification options can be applied during the forming process without requiring post-processing.

In an embodiment, the number of structural modifications is at least partly formed by forming a local protrusion at one or more walls forming the grid pattern. For example, the protrusion may extend within the plane in which the grid pattern extends two-dimensionally. Optionally, the protrusion may extend across more than one walls. In this way, the overall function of the anti-scatter grid is not disturbed by the number of structural modifications, wherein all these modification options can be applied during the forming process without requiring post-processing.

According to an embodiment, the number of structural modifications is at least partly formed by a local material recess at the grid pattern. For example, the material recess may be located at an edge, corner, etc. formed by the walls. In this way, the overall function of the anti-scatter grid is not disturbed by the number of structural modifications, wherein all these modification options can be applied during the forming process without requiring post-processing.

In an embodiment, the anti-scatter grid and/or grid pattern may comprise an area of interest and a periphery at least partially circumventing the area of interest; wherein the number of structural modifications may be formed on the periphery; and wherein a shape and/or dimension of individual ones of the number of structural modifications is varied to form the identification pattern.

As used herein, the area of interest may be understood as an area or region to be regularly used for a radiographic exposure reaching a detector. In this regard, the area of interest of the anti-scatter grid may also be referred to as an active area with respect to intended radiographic exposure. Likewise, the periphery, which may be a boundary, edge, or the like, of the anti-scatter grid, may be understood as a non-active area, as it is regularly not intended for radiographic exposure. For example, the number of structural modifications may form a pinhole or cross-hair pattern, wherein some or all of the number of structural modifications differ in shape and/or dimensions from each other. Preferably, the number of structural modifications may be located outside the active area, i.e. the area of interest, of the grid pattern. For example, they may be located on circumferential edge running around the grid pattern. Further, the structural modifications may intentionally be located, shaped and/or dimensioned for using them for measurement of size, position and/or displacement of e.g. an X-ray focal spot. In this way, the overall function of the anti-scatter grid is not disturbed by the number of structural modifications, wherein all these modification options can be applied during the forming process without requiring post-processing. Further, the identification pattern can also be used for e.g. focal spot measurement.

According to an embodiment, the number of structural modifications may at least partly be formed by locally applying a second material different to a first material used to form the grid pattern to appear differently in image data. It is noted that the grid pattern may still be formed by using one or more other materials besides the first material, so that this is not limited to one single material. The second material may be selected to provide, preferably well-defined, recognizable changes in optical or radiological image properties. The second material may be e.g. a light reflecting aluminum, or a non-X-ray absorbing polymer, e.g. arranged in a number of grid pixels. In this way, the anti-scatter grid can be read-out directly by the radiographic imaging device, e.g. an X-ray device, for which it is provided. Further, these modifications can be embedded into the anti-scatter grid without changing an outer structure of the grid pattern, even when an optical image is used, as the second material may also be applied near the surface without protruding from it.

In an embodiment, the identification pattern may comprise at least one partial pattern that is redundant within the identification pattern. For example, the identification pattern may comprise at least one 2-fold or 4-fold symmetry, or the like. This enhances detectability of the identification pattern within an X-ray image or optical image used to read it out, if the image has been acquired under largely different exposure conditions, e.g. low X-ray intensity, large focal spot, system vibrations or movements, etc.

According to a second aspect, there is provided a method for making a specific anti-scatter grid identifiable among one or more others, the anti-scatter grids being manufactured by an additive manufacturing process. The method may be applied to an anti-scatter grid manufactured by the method according to the first aspect. The method comprises the steps of:

capturing, by an imaging device, the specific anti-scatter grid in image data;
processing, by a data processing unit, the captured image data to extract an identification pattern formed by a number of structural modifications formed in addition to a grid pattern, formed by the additive manufacturing process in accordance with a product specification of the anti-scatter grid; generating, by the data processing unit, based on the extracted identification pattern, a unique identifier data assigned to the specific anti-scatter grid; and
recording the unique identifier data in relationship to the specific anti-scatter grid.

For example, the capturing of the image data may be performed in a viewing direction along a thickness direction of the anti-scatter grid, e.g. along a direction perpendicular to the plane in which the anti-scatter grid extends two-dimensionally.

Further, the processing of the captured image data may comprise one or more image analysis techniques, such as feature or pattern recognition, or the like.

For example, the generation of the identifier data may be random, based on a product code assignment, or the like.

Further, the recording of the unique identifier data may be stored as a data set in a storage medium. Further, it may be stored in a memory, a database, or the like.

According to an embodiment, the imaging device may be a radiographic imaging device. The radiographic imaging device may comprise a radiation source and a detector, wherein the anti-scatter grid is arranged between the radiation source and the detector when used as intended or when used in or with the radiographic imaging device. For example, the number of structural modification may be at least partly formed a local application of a second 3D printing material which provides well-defined changes in X-ray and/or optical properties, wherein the second 3D printing material may be e.g. light reflecting aluminum, or a non-X-ray absorbing polymer, e.g. located in a number of anti-scatter grid pixels. In this way, the identification pattern can be read-out in the device intended according to the specification, in which it is already installed.

According to a third aspect, there is provided an anti-scatter grid for a radiographic imaging device. The anti-scatter grid comprises:

a grid pattern, formed by an additive manufacturing process in accordance with a product specification of the anti-scatter grid; and
an identification pattern, configured to be recognizable by an imaging device when the anti-scatter grid is viewed according to its intended use in viewing direction from a radiation source, and formed by a number of structural modifications formed in addition to the grid pattern by the additive manufacturing process.

For example, the anti-scatter grid may be manufactured by carrying out the method according to the first aspect. Further, the anti-scatter grid may be configured to be read-out to obtain its unique identifier by applying the method according to the second aspect and/or using the device according to the fourth aspect.

The anti-scatter grid provides at least largely corresponding technical effects as described above with respect to the first aspect.

According to a fourth aspect, there is provided a device for identifying a specific anti-scatter grid among one or more others. For example, the device may be configured to read-out the identification pattern generated by the method of the first aspect, to carry out the method according to the second aspect, and to be applied to the anti-scatter grid according to the third aspect. The device comprises:

a data processing unit, configured to:
obtain image data of the specific anti-scatter grid, the anti-scatter grid being viewed according to its intended use in a viewing direction from a radiation source;
process the obtained image data to extract an identification pattern formed by a number of structural modifications formed in addition to a grid pattern, formed in accordance with a product specification of the anti-scatter grid;
generate, based on the extracted identification pattern, a unique identifier data assigned to the specific anti-scatter grid; and record the identifier data in relationship to the specific anti-scatter grid.

For example, the data processing unit may be any computational means, such as a processor, or the like.

The image data may be provided by an imaging device, such as optical imaging device, e.g. a camera, or a radiological device, e.g. an X-ray device. For example, the image data may be optical image data, a radiological image, etc.

The device provides technical effects at least largely corresponding to that described above with reference to the second aspect, so this will not be repeated here.

According to an embodiment, the data processing unit may be further configured to: obtain software application program data dedicated to the specific anti-scatter grid and comprising a unique software identifier data;

compare the unique software identifier data with the unique identifier data assigned to the specific anti-scatter grid; and block access to the software application if there is no match between the compared identifier data, or allow access to the software application if there is a match between the compared identifier data.

For example, the software application program may be intended and/or configured to be operated only in combination with the specific anti-scatter grid, meaning that operating it in combination with an anti-scatter grid having a different unique identification pattern or that is missing the same at all is permitted. In this way, a user access protection is provided.

In an embodiment, the data processing unit may be further configured to obtain, based on the identifier data of the specific anti-scatter grid, a calibration data set dedicated to the specific anti-scatter grid and configured to calibrate a radiographic imaging system for the specific anti-scatter grid.

A fifth aspect is directed to the use of the anti-scatter grid according to the third aspect for product activation. In other words, the unique identification pattern of the anti-scatter grid may also be understood as a product key allowing a license validation procedure. Such a procedure is described above with reference to the fourth aspect. Therefore, another aspect is directed to the use of the anti-scatter grid according to the third aspect in a license validation procedure. The product to be activated may be the software application described above with reference to the fourth aspect.

According to a sixth aspect, there is provided a computer program element, which when executed by a processor is configured to carry out the method of the first or second aspect, and/or to control a device or system according to the fourth aspect.

According to a seventh aspect, there is provided a computer-readable storage or transmission medium, which has stored or which carries the computer program element according to the sixth aspect.

It is noted that the above embodiments may be combined with each other irrespective of the aspect involved. Accordingly, the method may be combined with structural features of the device and/or system of the other aspects and, likewise, the device and the system may be combined with features of each other, and may also be combined with features described above with regard to the method.

These and other aspects of the present invention will become apparent from and elucidated with reference to the embodiments described hereinafter.

BRIEF DESCRIPTION OF THE DRAWINGS

Exemplary embodiments of the invention will be described in the following drawings.

DETAILED DESCRIPTION OF EMBODIMENTS

Figure 1:
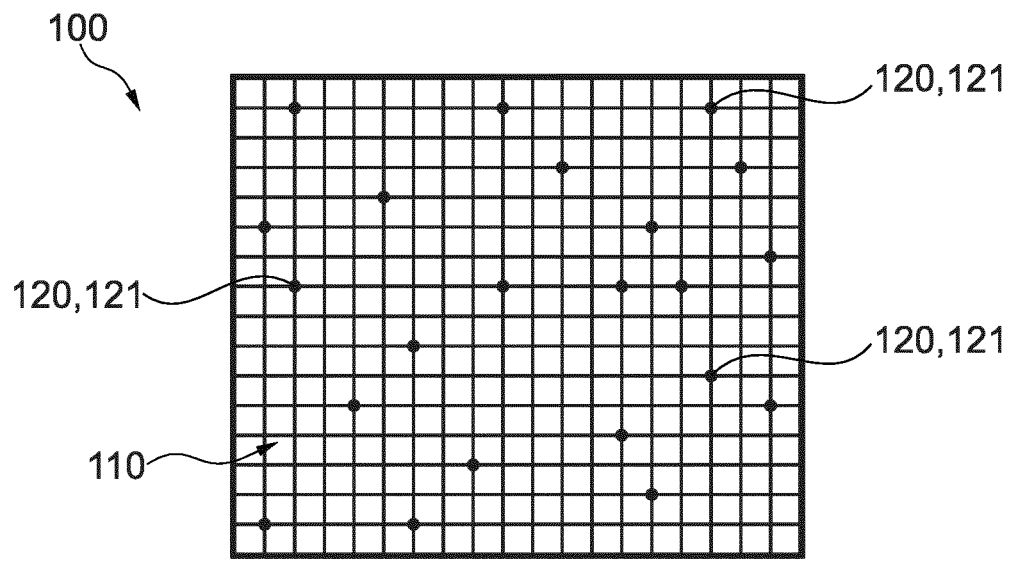
FIG. 1 shows in a schematic plan or top view an anti-scatter grid according to an embodiment.

FIG. 1 shows in a schematic plan or top view an exemplary anti-scatter grid 100 according to an embodiment. For example, the anti-scatter grid 100 may be used for limiting an amount of radiation scatter reaching a detector of a radiographic imaging device, such as an X-ray device, gamma ray device, or other ionizing radiation utilizing device. In its intended use, the anti-scatter grid 100 is preferably arranged and/or positioned between a radiation source and the detector of the radiographic imaging device. In particular, the anti-scatter grid may be positioned on an opposite side of a subject to be imaged from the radiation source, and between the subject and the detector.

The anti-scatter grid 100 comprises a grid pattern 110, which is formed by a plurality of parallel walls, also referred to as septa walls, made of a radiation, e.g. X-ray, absorbing material, such as tungsten, lead, etc., and a radiation non-absorbing, e.g. radiolucent, material, such as a plastic, carbon fibre, aluminum, paper, etc. The grid pattern 110 forms a plurality of grid pixels.

As will be explained in more detail below, the grid pattern 110 is formed by an additive manufacturing process in accordance with a product specification of the anti-scatter grid 100. Thereby, one or more anti-scatter grids 100 may be formed according to a first product specification, one or more anti-scatter grids 100 may be formed according to at least one further, second, third, etc. product specification, wherein it is desirable that all anti-scatter grids 100 manufactured according to a common product specification are distinguishable from each other, as well as being distinguishable from all anti-scatter grids 100 manufactured according to one or more further product specifications. For example, the product specification may comprise information about a structure of the anti-scatter grid 100, e.g. dimensions, arrangement of walls, choice of materials, etc. Thereby, the product specification may define a specific type of anti-scatter grid and/or an anti-scatter grid that is dedicated to a specific radiographic imaging device.

Further, the anti-scatter grid 100 comprises an identification pattern 120, which is formed by a number, preferably by multiple or by a plurality of, structural modifications 121 formed in addition to the grid pattern 110. In other words, some, e.g. a subset, or all of the number of structural modifications 121 together form the additional identification pattern 120. In at least some embodiments, the identification pattern 120 may be located within the grid pattern 110, as exemplary shown in FIG. 1. The identification pattern 120 is configured to be recognizable by an imaging device when the anti-scatter grid 100 is viewed according to its intended use in viewing direction from a radiation source, as will be explained in more detail below.

Although FIG. 1 shows, only by way of example, the number of structural modifications 121 by identically illustrated points (only some of which are denoted by the reference sign 121 for clarity), it should be noted that one or more, or each, of the number of structural modifications 121 may also differ structurally from one another. Further, the number of structural modifications 121 may also be arranged on the same walls, and may otherwise be freely configurable, provided that the resulting identification pattern 120 is unique. In other words, each identification pattern 120 provided to a specific one anti-scatter grid 100 has its unique combination formed from the number of modifications 121, so that no identification pattern 120 is the same as the others, but differs from all the others in at least one combination point, i.e. in at least one structural modification 121, and is thus uniquely identifiable. Thereby, each of the number of modifications 121 may be varied in e.g. its location, dimensions, shape and/or type, etc.

Further, as will be explained in more detail below, the identification pattern 120 and/or the number of structural modifications 121 is formed by an additive manufacturing process, which may be same, i.e. in terms of the basic technique used in the process, as for forming the grid pattern 110, or may be different thereto. For example, the grid pattern 110 may be formed by a first type of additive manufacturing process, and the identification pattern 120 may be formed by second type of additive manufacturing process, wherein the first and second type may be identical or different to each other. Further, in at least some embodiments, the identification pattern 110 may be formed during the forming the grid pattern 110, i.e. during carrying out the first type of additive manufacturing process.

It is noted that the identification pattern 120 is unique for each anti-scatter grid 100 manufactured and/or provided, so as to create an unique identifier to make the anti-scatter grid to be provided identifiable among one or more others, even if these are manufactured according to a common underlying product specification. In other words, the identification pattern 120 may be understood as an unique identifier, e.g. a watermark, that allows to record an one-to-one-correspondence with the associated anti-scatter grid 100. The identification pattern 120 may be read-out and processed electronically at both the physical anti-scatter grid 100 and an electronic record indicating the identification pattern 120 or its identifier.

In the following, exemplary embodiments relating to a design of the number of structural modifications 121 are explained below, wherein each of these embodiments may be formed alone or may be combined with one or more of the others, to form the identification pattern 120.

Optionally, the number of structural modifications 121 is at least partly formed by locally shifting one or more walls forming the grid pattern 110. For example, a section of a wall may be brought out of alignment with adjacent sections so that this is visually recognizable.

Optionally, the number of structural modifications 121 is at least partly formed by forming a local variation of thickness of one or more walls forming the grid pattern. For example, an additional amount of material may be, preferably slightly, thickened at the corresponding location. Preferably, the additional amount of material may be located in a corner between two walls.

Optionally, the number of structural modifications 121 is at least partly formed by a local material recess at the grid pattern 110. For example, the material recess may be located at an edge, corner, etc. formed by the walls.

Optionally, the identification pattern 120 comprises at least one partial pattern, e.g. a subset of the structural modifications 121, that is redundant within the identification pattern. That is, one or more combinations of at least a subset of structural modifications 121 are formed at least twice, three times, four times, etc. For example, the identification pattern may comprise at least one 2-fold or 4-fold symmetry, or the like.

Further optionally, the number of structural modifications 110 is at least partly formed by locally applying a second material different to a first material used to form the grid pattern to appear differently in image data. The second material may be selected to provide, preferably well-defined, recognizable changes in optical or radiological image properties. The second material may be e.g. a light reflecting aluminum, or a non-X-ray absorbing polymer, e.g. arranged in a number of grid pixels.

Figure 2:
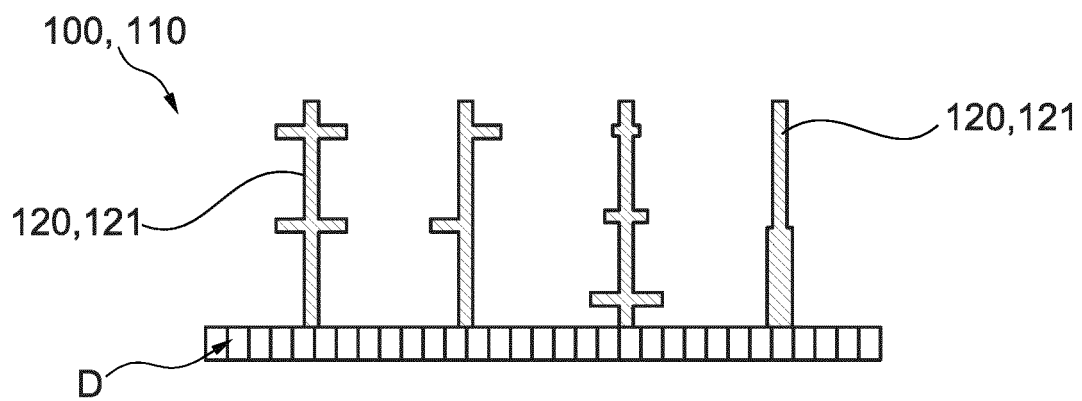
FIG. 2 shows in a schematic side view a section of an anti-scatter grid according to an embodiment, comprising a number of structural elements having exemplary shapes, dimensions, orientations, etc.

FIG. 2 shows in a schematic side view, in some kind of partial cross-section, at least a section of the anti-scatter grid 100 according to an exemplary embodiment. In particular, FIG. 2 shows further exemplary embodiments relating to the design of the number of structural modifications 121, wherein each of these embodiments may be formed alone or may be combined with one or more of the others, and/or may be combined with those described above with reference to FIG. 1, to form the identification pattern 120. The design of the structural modifications 121 may be varied in terms of shape, dimensions, orientation, location, pattern of protrusion or recesses, material, or the like, as described herein.

Further, FIG. 2 indicates an exemplary detector D with a pixel-array of a radiographic imaging device, a preferred application of the anti-scatter grid 100, wherein the detector D with reference to the sheet plane of FIG. 2 is arranged below the structural modifications 121. In addition, FIG. 2 illustrates exemplary orientations, geometries, shapes, or the like, of the structural modifications 121.

Figure 3:
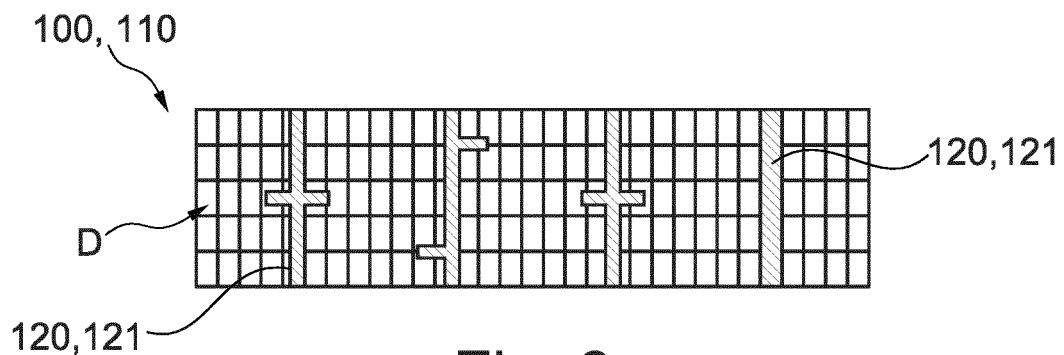
FIG. 3 shows in a schematic plan or top view the section of an anti-scatter grid of FIG. 2.

Likewise, FIG. 3 shows in a schematic plan or top view the section of the anti-scatter grid 100 as shown in FIG. 2 in the schematic side view. Preferably, FIG. 2 and FIG. 3 may refer to the same one or more walls. Referring to FIG. 3, the design of the number of structural modifications 121 may be varied in terms of shape, dimensions, orientation, location, pattern of protrusion or recesses, material, or the like, as described herein. Thereby, each of these embodiments may be formed alone or may be combined with one or more of the others, and/or may be combined with those described above with reference to FIGS. 1 and 2, to form the identification pattern 120.

Further, FIG. 3 also indicates the pixel-array of detector D, arranged below the structural modifications 121 with reference to the sheet plane of FIG. 3.

According to FIG. 2 and/or FIG. 3, further optionally, the number of structural modifications 121 is at least partly formed by forming a local protrusion at one or more walls forming the grid pattern 110. For example, such a protrusion may extend within the plane in which the grid pattern extends two-dimensionally. Optionally, such a protrusion may extend across more than one walls. By way, of examples the one or more local protrusions, i.e. the number of structural modifications according to this embodiment, may be formed as, preferably small, well-defined protrusions located in, on top, or at bottom of the walls of the grid pattern 110, wherein FIG. 2 exemplary shows different configurations, of which one or more may be selected.

Figure 4:
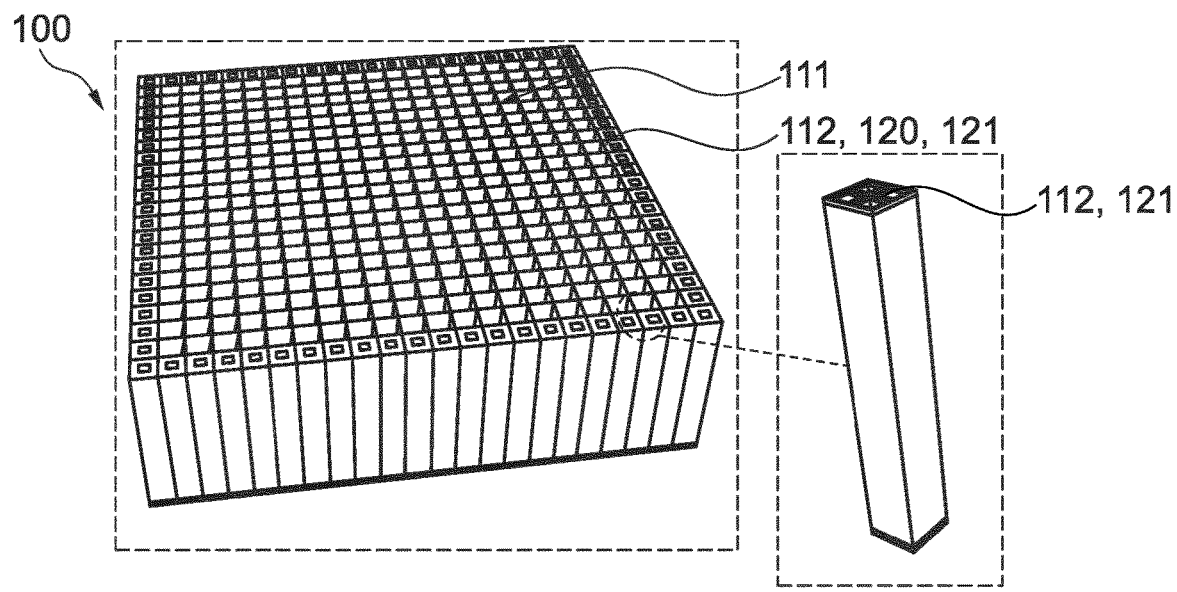
FIG. 4 shows in a schematic perspective view an anti-scatter grid, according to an embodiment.

FIG. 4 shows in a schematic perspective view an exemplary embodiment of the anti-scatter grid 100. In this embodiment, the anti-scatter grid 100 and/or the grid pattern 100 comprises an area of interest 111 and a periphery 112 at least partially circumventing the area of interest 111. Thereby, the number of structural modifications 121 is formed on the periphery 112, i.e. outside the area of interest 111, for example, located on a circumferential edge running around the grid pattern 110. A shape and/or a dimension, or the like, of individual ones of the number of structural modifications 121 is varied to form the identification pattern 120 in a unique manner. For example, the number of structural modifications 121 may form a pinhole or cross-hair pattern, wherein some or all of the number of structural modifications 121 differ in shape and/or dimensions from each other.

Further, in at least some embodiments, the structural modifications 121 may be intentionally located, shaped and/or dimensioned for using them for measurement of size, position and/or displacement of e.g. an X-ray focal spot.

Figure 5:
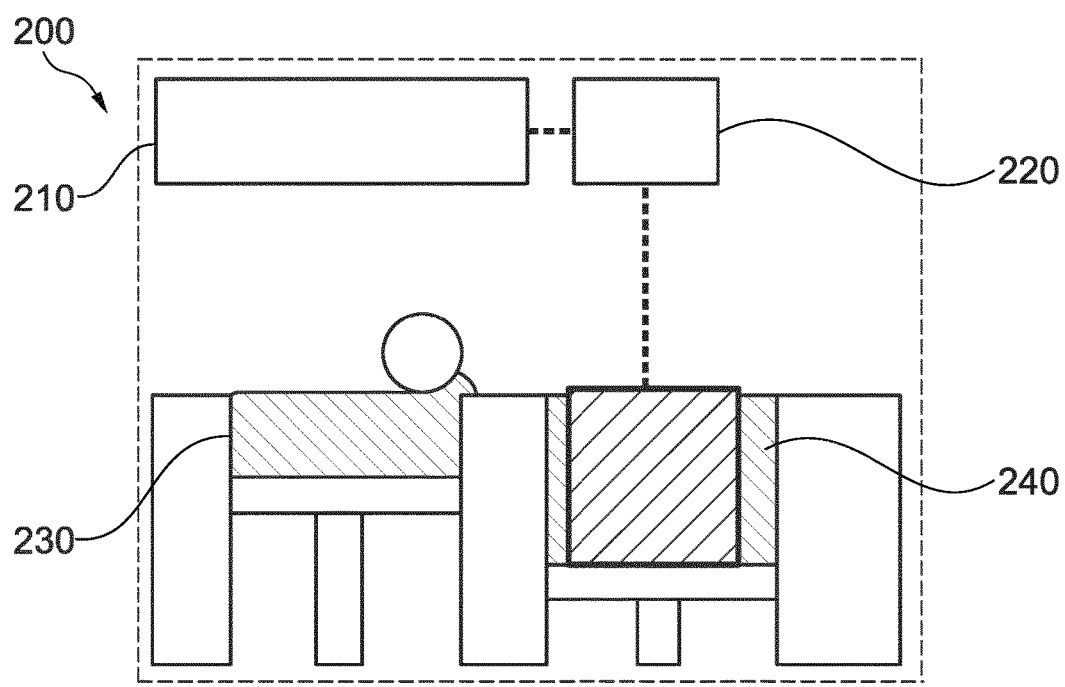
FIG. 5 shows an exemplary 3D printing device to be used for providing an anti-scatter grid according to an embodiment.

FIG. 5 shows an exemplary additive manufacturing device 200, e.g. a 3D printing device, which may be used to manufacture the anti-scatter grid 100 as described above. It is noted that although the additive manufacturing device 200 is exemplary shown as a direct metal laser sintering (DMLS) device, the it may alternatively be configured as a device for selective laser melting (SLM), selective laser sintering (SLS), electron-beam melting (EBM), or the like. This is not limited herein. As mentioned above, the grid pattern 110 and the number of structural modifications 121 may be formed by using different additive manufacturing processes or techniques, so that two or more different additive manufacturing devices 200 may be used to provide the anti-scatter grid 100.

The additive manufacturing device 200 may comprise, for example, a laser 210, coupled with a scanner system 220, a powder delivery system 230, and a powder forming system 240. Additive manufacturing devices in different configurations are known in the art, and the device's configuration can be selected in a manner suitable for the purpose described herein.

Figure 6:
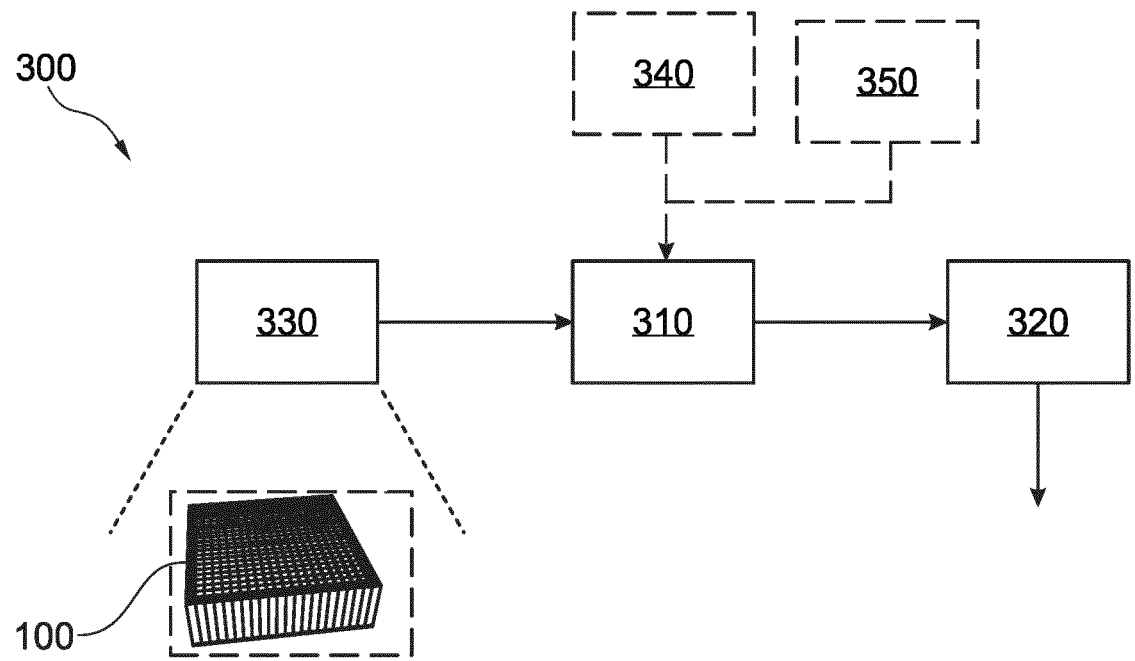
FIG. 6 illustrates in a schematic block diagram a product identification process utilizing an anti-scatter grid and a device for identifying the anti-scatter grid, according to an embodiment.

FIG. 6 illustrates in schematic block diagram a product identification process or method according to an embodiment, utilizing the anti-scatter grid 100 as described above and a device 300 for identifying the anti-scatter grid 100.

The device 300 is configured to identify a specific anti-scatter grid 100 among one or more others, either of the same type or of a different type. For example, the device 300 is configured to read-out the identification pattern 120 generated as described herein. The device 300 comprises at least a data processing unit 310 that is configured to obtain image data of the specific anti-scatter grid 100, wherein "specific" is to be understood that a one-by-one correspondence is to be made between the identification pattern 120 and the corresponding anti-scatter grid 100. The data processing unit 310 is further configured to process the obtained image data to extract the identification pattern 120 formed by the number of structural modifications 121 from the obtained image data. Further, the data processing unit 310 is configured to generate, based on the extracted identification pattern 120, corresponding unique identifier data assigned to the specific anti-scatter grid 100. The data processing unit 310 is further configured to record the identifier data in relationship to the specific anti-scatter grid, e.g. in a memory 320, a database, a server, or the like, in an electronic manner. The recorded identifier data may be used for product identification, product tracing, product copyright protection, product service, etc.

The image data may be provided by an imaging device 330, such as an optical imaging device, e.g. a camera, or a radiographic and/or radiological device, e.g. an X-ray device, etc. Accordingly, the image data may be optical image data, a radiological image, etc. In at least some embodiments, the imaging device 330 may be a radiographic imaging device comprising a radiation source and a detector. Thereby, in its intended use, the anti-scatter grid 100 is preferably arranged and/or positioned between the radiation source (not shown) and the detector. In particular, the anti-scatter grid 100 may be positioned on an opposite side of a subject to be imaged from the radiation source, and between the subject and the detector. And in this intended use, i.e., when so arranged, the anti-scatter grid 100 may be identified as described herein. Even by the radiographic imaging device itself in or with which it is intended to be or is used. Optionally, the number of structural modifications 121 may be at least partly formed by a local application of a second 3D printing material which provides well-defined changes in X-ray and/or optical properties, wherein the second 3D printing material may be e.g. light reflecting aluminum, or a non-X-ray absorbing polymer, e.g. located in a number of anti-scatter grid pixels.

Optionally, the data processing unit 310 is further configured to obtain software application program data 340 dedicated to the specific anti-scatter grid 100 and comprising unique software identifier data. Further, the data processing unit 310 is configured to compare the unique software identifier data with the unique identifier data assigned to the specific anti-scatter grid 100. Furthermore, the data processing unit 310 is configured to block access to the software application if there is no match between the compared identifier data, or allow access to the software application if there is a match between the compared identifier data.

Further optionally, the data processing unit 310 is further configured to obtain, based on the identifier data of the specific anti-scatter grid, a calibration data set 350 dedicated to the specific anti-scatter grid and configured to calibrate a radiographic imaging system for the specific anti-scatter grid.

In other words, the unique identification pattern of the anti-scatter grid may also be understood as a product key allowing a license validation procedure, and/or an compensation or calibration procedure.

Figure 7:
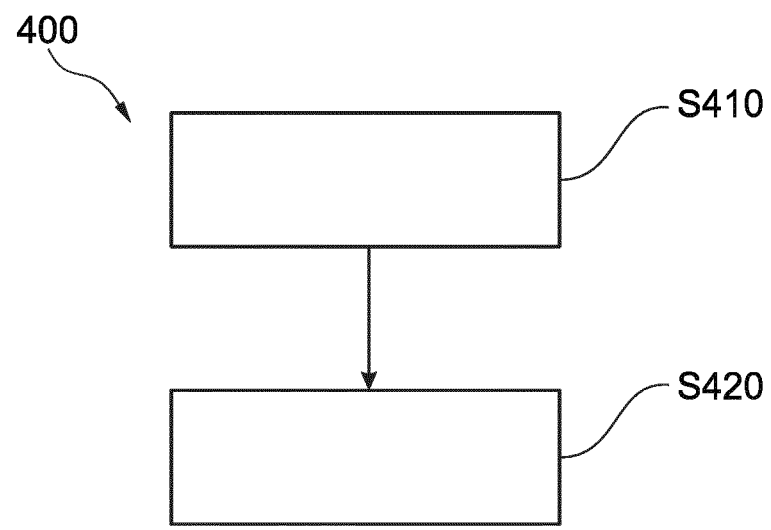
FIG. 7 shows in a flow chart a method for providing an anti-scatter grid for a radiographic imaging device, according to an embodiment.

FIG. 7 shows in a flow chart a method 400 for providing the anti-scatter grid 100. The method may be performed by using the device 200 as described above. The method 400 comprises the following steps.

In a step S410, the grid pattern 110 is formed by an additive manufacturing process, wherein the grid pattern 110 is formed in accordance with a corresponding product specification of the anti-scatter grid 100 to be provided.

In a step S420, the number of structural modifications 121 is formed, by the same or another additive manufacturing process, in or at the grid pattern 110 in a manner making the number of structural modifications 121 image-based recognizable and in the unique identification pattern 120, thereby creating a unique identifier to make the anti-scatter grid 100 to be provided identifiable among one or more others.

Figure 8:
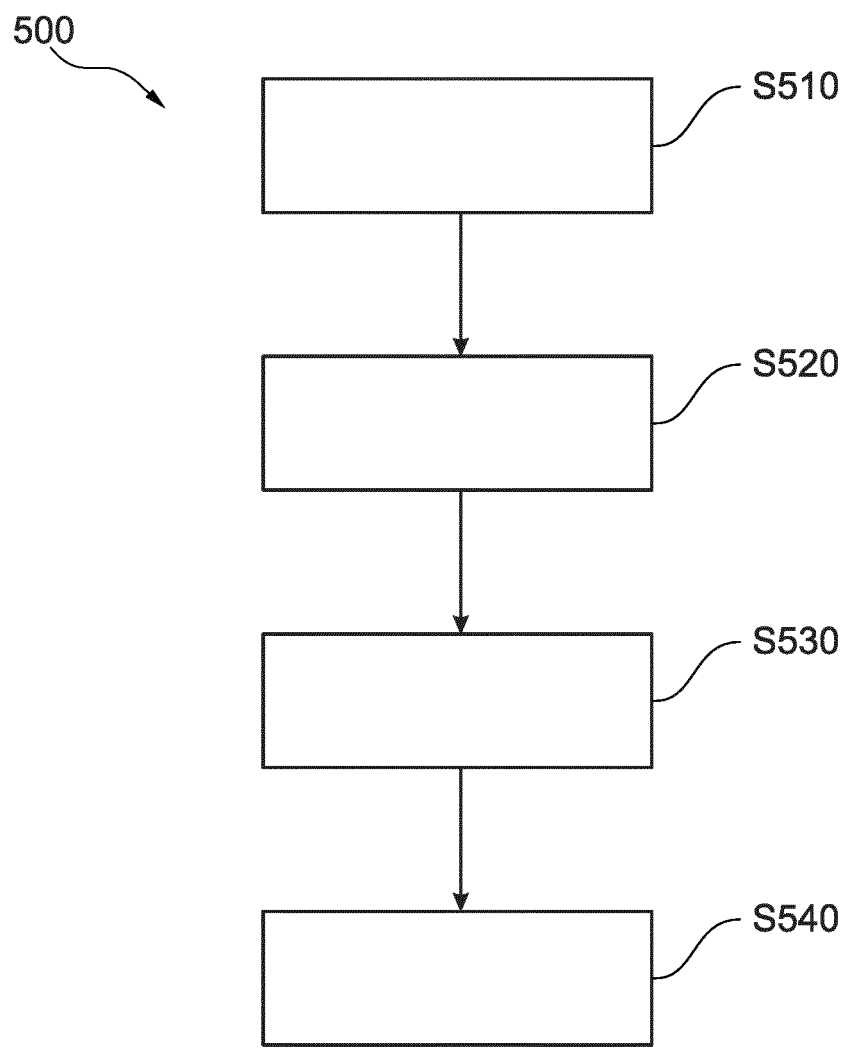
FIG. 8 shows in a flow chart a method for making a specific anti-scatter grid identifiable among one or more others, according to an embodiment.

FIG. 8 shows in a flow chart a method 500 for making a specific one anti-scatter grid 100 identifiable among one or more others. The method may be carried out by the device 300 as described above. The method comprises the steps of:

A step S510 comprises capturing, by the imaging device 330, the specific anti-scatter grid 100 in image data.

A step S520 comprises processing, by the data processing unit 310, the captured image data to extract the identification pattern 320 formed by a number of structural modifications formed in addition to a grid pattern, formed by the additive manufacturing process in accordance with a product specification of the anti-scatter grid 100;

A step S530 comprises generating, by the data processing unit 310, based on the extracted identification pattern 120, a unique identifier data assigned to the specific anti-scatter grid 100; and A step S540 comprises recording, e.g. in the memory 320, database, server, etc., the unique identifier data in relationship to the specific anti-scatter grid.

It is noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and the foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS 100 anti-scatter grid
110 grid pattern
111 region of interest
112 periphery
120 identification pattern
121 structural modification
200 manufacturing device
2xx component of device
300 device, e.g. watermark reader
310 data processing unit
320 storage
330 imaging device
340 data set
350 data set
D detector
4xx method (step)
5xxx method (step)

The invention claimed is:

1. A method for providing an anti-scatter grid for a radiographic imaging device, the method comprising:
    forming, by an additive manufacturing process, a grid pattern in accordance with a product specification of the anti-scatter grid to be provided; and
    forming, by an additive manufacturing process, a number of structural modifications in or at the grid pattern in a manner making the number of structural modifications image-based recognizable when the anti-scatter grid is viewed according to its intended use in a viewing direction from a radiation source of the radiographic imaging device, and in a unique identification pattern creating a unique identifier to make the anti-scatter grid to be provided identifiable among one or more others.

2. The method of claim 1, wherein the number of structural modifications is formed to be recognizable by forming at least a part of the number of structural modifications at one or more walls and/or surfaces forming the grid pattern.

3. The method of claim 1, wherein the number of structural modifications is at least partly formed by locally shifting one or more walls forming the grid pattern.

4. The method of claim 1, wherein the number of structural modifications is at least partly formed by forming a local variation of thickness of one or more walls forming the grid pattern.

5. The method of claim 1, wherein the number of structural modifications is at least partly formed by forming a local protrusion at one or more walls forming the grid pattern.

6. The method of claim 1, wherein the number of structural modifications is at least partly formed by a local material recess at the grid pattern.

7. The method of claim 1, wherein the grid pattern comprises an area of interest and a periphery at least partially circumventing the area of interest; wherein the number of structural modifications is formed on the periphery; and wherein a shape and/or dimension of individual ones of the number of structural modifications is varied to form the identification pattern.

8. The method of claim 1, wherein the number of structural modifications is at least partly formed by locally applying a second material different to a first material used to form the grid pattern to appear differently in image data.

9. The method of claim 1, wherein the identification pattern comprises at least one partial pattern that is redundant within the identification pattern.

10. A method for making a specific anti-scatter grid identifiable among one or more others, the anti-scatter grids being manufactured by an additive manufacturing process, the method comprising:
    capturing, by an imaging device, the specific anti-scatter grid in image data, the anti-scatter grid being viewed according to its intended use in a viewing direction from a radiation source;
    processing, by a data processing unit, the captured image data to extract an identification pattern formed by a number of structural modifications formed in or at a grid pattern formed by the additive manufacturing process in accordance with a product specification of the anti-scatter grid;
    generating, by the data processing unit, based on the extracted identification pattern, a unique identifier data assigned to the specific anti-scatter grid; and
    recording the unique identifier data in relationship to the specific anti-scatter grid.

11. The method of claim 10, wherein the imaging device is a radiographic imaging device.

12. A device for identifying a specific anti-scatter grid among one or more others, the device comprising:
    a data processing unit, configured to:
        obtain image data of the specific anti-scatter grid, the anti-scatter grid being viewed in viewing direction from a radiation source in accordance with its intended use;
        process the obtained image data to extract an identification pattern formed by a number of structural modifications formed in or at a grid pattern, formed in accordance with a product specification of the anti-scatter grid;

generate, based on the extracted identification pattern, a unique identifier data assigned to the specific anti-scatter grid; and record the identifier data in relationship to the specific anti-scatter grid.

13. The device of claim 12, wherein the data processing unit is further configured to:

obtain software application program data comprising a unique software identifier data;

compare the unique software identifier data with the unique identifier data assigned to the specific anti-scatter grid; and block access to the software application if there is no match between the compared identifier data, or allow access to the software application if there is a match between the compared identifier data.

14. The device of claim 12, wherein the data processing unit is further configured to obtain, based on the identifier data of the specific anti-scatter grid, a calibration data set dedicated to the specific anti-scatter grid and configured to calibrate an imaging system for the specific anti-scatter grid.

\* \* \* \* \*